United States Patent [19]
Kruse et al.

[11] Patent Number: 5,571,833
[45] Date of Patent: Nov. 5, 1996

[54] TRYPTAMINE ANALOGUES, THEIR SYNTHESIS AND THEIR USE AS 5-HT$_1$-LIKE OR 5-HT$_2$ RECEPTOR AGONISTS

[75] Inventors: Lawrence I. Kruse, Haddonfield, N.J.; Rodney C. Young, Hertford; Alberto J. Kaumann, Trumpington, both of England

[73] Assignee: SmithKline Beecham plc, England

[21] Appl. No.: 167,890

[22] PCT Filed: Jun. 17, 1992

[86] PCT No.: PCT/GB92/01089

§ 371 Date: May 26, 1994

§ 102(e) Date: May 26, 1994

[87] PCT Pub. No.: WO93/00333

PCT Pub. Date: Jan. 7, 1993

[30] Foreign Application Priority Data

Jun. 21, 1991 [GB] United Kingdom ............ 9113382
Jun. 21, 1991 [GB] United Kingdom ............ 9113385

[51] Int. Cl.$^6$ ................... A61K 31/40; C07D 207/08
[52] U.S. Cl. ................ 514/414; 514/415; 548/468; 548/504
[58] Field of Search ................... 548/504, 468; 514/415, 414

[56] References Cited

FOREIGN PATENT DOCUMENTS

| | | | |
|---|---|---|---|
| 58-083671 | 5/1983 | Japan | 548/504 |
| WO-A-9005721 | 5/1990 | WIPO | 548/504 |

OTHER PUBLICATIONS

CA 81:105166j Synthesis . . . 2–(2–aminopropyl) indoles. Bhat et al., p. 497, 1974.
CA83:147449a Synthesis . . . indoles. Bhat et al., p. 497, 1975.
CA85:21176g Synthesis . . . agent. Hiremath et al., p. 675, 1976.
CA96:20117d Amidines, . . . use. Renner et al., p. 456, 1982.
Patent Abstracts of Japan C–179 7175 3 Mar. 83.
Chem. Abs. vol. 110, No. 3, 16 Jan. 89, abs. No. 187733d, Shabunina et al, Prevention of arrhythmias in acute ischaemia in conscious animals with a serotonin analog.
Chem Pharm Bull vol. 36, No. 3, 1988, pp. 1162–1168 Somei et al.
Advan Pharmacol, vol. 6B 1968, 233–246, Cerletti et al.
Comp Biochem Physiol C, vol. 69C, No. 2, 1981, 359–366, Landau et al.
Nature, vol. 316, No. 6024, 11 Jul. 1985, 126–131, Richardson et al.
J. Org. Chem. vol. 52, No. 13, 26 Jun. 1987, 2817–2825. Wrona M Z & Dryhurst G.

*Primary Examiner*—Joseph McKane
*Attorney, Agent, or Firm*—Nora Stein-Fernandez; William T. King; Edward T. Lentz

[57] ABSTRACT

The present invention relates to known and novel tryptamine analogues, processes and intermediates useful in their preparation, pharmaceutical compositions containing them and their use in therapy, in particular for the treatment and/or prophylaxis of disorders characterized by excessive vasodilatation, such as migraine and portal hypertension.

11 Claims, No Drawings

TRYPTAMINE ANALOGUES, THEIR SYNTHESIS AND THEIR USE AS 5-HT$_1$-LIKE OR 5-HT$_2$ RECEPTOR AGONISTS

This application is a 371 of PCT/GB92/01089 filed Jun. 17, 1992.

The present invention relates to known and novel tryptamine analogues, processes and intermediates useful in their preparation, pharmaceutical compositions containing them and their use in therapy, in particular for the treatment and/or prophylaxis of disorders characterised by excessive vasodilatation, such as migraine and portal hypertension.

Migraine is a non-lethal disease suffered by one in ten individuals. The main symptom is headache; other symptoms include vomiting and photophobia. Currently, the most widely used treatment for migraine involves administration of ergotamine, dihydroergotamine or methysergide. All these drugs are inter alia agonists of 5HT$_1$-like receptors but also have other actions; treatment with them is associated with a number of adverse side effects. In addition, some patients experience a "withdrawal headache" following the cessation of treatment with an ergot product, such as ergotamine, causing them to repeat the treatment and resulting in a form of addiction. More recently a variety of tryptamine derivatives have been proposed for potential use in the treatment of migraine.

Portal hypertension, which is commonly associated with cirrhosis of the liver is characterised by increased portal venous blood flow, (which is caused by dilatation of mesenteric arterioles), and increased portal vascular resistance. A serious complication of this condition is rupture of oesophageal varices or paraesophageal collaterals, which develop to reduce portal pressure.

Japanese Published Application No. J58-83671 (Mitsui Toatsu Chem Inc) describes a process for preparing compounds of the formula:

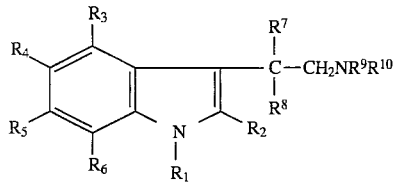

wherein $R_{1-10}$ represent hydrogen, halogen, hydroxyl, alkoxy, cyano, acyl, aryl or alkyl; and $R_7$ and $R_8$ or $R_9$ and $R_{10}$ may be linked by a saturated or unsaturated carbon chain. In the compounds specifically exemplified $R^3$, $R^5$ and $R^6$ are hydrogen and $R^4$ is hydrogen or methoxy. The compounds are said to have physiological activity, but no specific utility is described.

PCT Application WO 90/05721 describes a class of α-amino-indole-3-acetic acids which are said to be useful as antidiabetic, antiobesity and anti-atherosclerotic agents. The compounds are represented by the general formula:

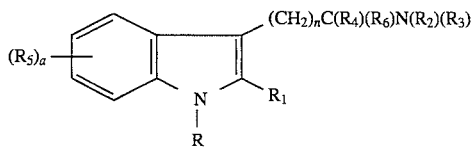

and the values of $R-R_6$ may be chosen from many possibilities. Thus R, $R_1$, $R_3$ and $R_4$ may be inter alia hydrogen; $R_6$ is inter alia hydrogen or alkyl; $R_2$ is inter alia alkyl; $R_5$ is inter alia hydrogen, halogen, hydroxy, alkoxy, nitro, CN or CF$_3$; a is 1–4 and n is 0 or 1. All the compounds specifically disclosed are derivatives of indole-3-acetic acid or tryptophan.

The compound 3-(2-aminoethyl)-4-chloro-5-hydroxyindole is described as a putative intermediate in the oxidation of 5-hydroxytryptamine (Wrona and Dryhurst, J. Org. Chem 1987, 52, 2817–2825. 4-Methyl-5-hydroxytryptamine and its actions at 'D' and 'M' receptors are described by Richardson et al, Nature, 316(6024), 126–131, 1985.

We have now surprisingly found that certain 4,5-substituted tryptamines not specifically disclosed in J 58–83671 or WO 90/05721 are agonists at 5-HT$_1$-like and/or 5-HT$_2$ receptors and are expected to have utility in the treatment of conditions where such agonists are indicated, such as the treatment or prophylaxis of migraine or the treatment of portal hypertension. In this specification the term agonist also includes partial agonists.

The present invention therefore provides, in a first aspect, the use of a compound of structure (I):

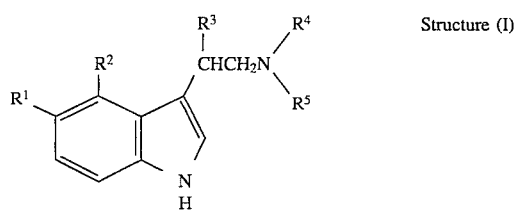

Structure (I)

in which $R^1$ is hydrogen, hydroxy, C$_{1-4}$alkoxy, halo C$_{1-4}$alkoxy, C$_{3-7}$cycloalkyl-C$_{1-4}$alkoxy, aryloxy or arylC$_{1-4}$alkoxy;

$R^2$ is halogen, C$_{1-4}$alkyl, CN, NO$_2$ or CF$_3$;

$R^3$ is hydrogen or C$_{1-4}$alkyl;

$R^4$ and $R^5$ are the same or different and are each hydrogen or C$_{1-4}$alkyl or together with the nitrogen atom to which they are attached form a ring;

and pharmaceutically acceptable salts, solvates and hydrates thereof; for the manufacture of a medicament for the treatment of conditions where a 5-HT$_1$-like or 5-HT$_2$ agonist is indicated, in particular the treatment and prophylaxis of migraine, or the treatment of portal hypertension.

In a further aspect the present invention also provides novel compounds of structure (I) and salts, solvates and hydrates thereof, wherein $R^1$ $R^2R^3$ $R^4$ and $R^5$ are as defined above, with the provisos that:

(i) when $R^1$ is hydroxy and $R^3$, $R^4$ and $R^5$ are each hydrogen then $R^2$ is not chloro, or methyl;

(ii) when $R^1$ is methoxy and $R^3$, $R^4$ and $R^5$ are each hydrogen then $R^2$ is not NO$_2$; and (iii) when $R^1$, $R^3$, $R^4$ and $R^5$ are each hydrogen then $R^2$ is not bromo, chloro, CN or methyl.

In the compounds of structure (I) C$_{1-4}$alkyl groups (alone or as part of another group, e.g. C$_{1-4}$alkoxy) can be straight or branched. A halo C$_{1-4}$alkyl group signifies C$_{1-4}$alkyl completely or partially substituted by halogen.

$R^1$ is suitably hydrogen, hydroxy, C$_{1-4}$alkoxy, C$_{1-4}$alkoxy completely or partially substituted by halogen, in particular fluorine, aryloxy or arylC$_{1-4}$alkoxy. Preferably $R^1$ is hydroxy, C$_{1-4}$alkoxy or arylC$_{1-4}$alkoxy. Most preferably $R^1$ is C$_{1-4}$alkoxy.

Suitably, $R^2$ is halogen, C$_{1-4}$alkyl, CN, NO$_2$ or CF$_3$. Preferably $R^2$ is halogen, in particular chlorine.

Suitably, $R^3$ is hydrogen or C$_{1-4}$alkyl. Preferably $R^3$ is hydrogen.

Suitably, $R^4$ and $R^5$ are the same or different and are each hydrogen or C$_{1-4}$alkyl or together with the nitrogen atom to which they are attached form a ring. Preferably $R^4$ and $R^5$ are each hydrogen or $C_{1-4}$alkyl, e.g. methyl.

Suitable rings formed by $R^4$ and $R^5$ together with the nitrogen atom to which they are attached include for, example, 5- or 6-membered rings such as pyrrolidino and piperidino rings.

Particular compounds of structure (I) include: 3-(2-(aminoethyl)-4-chloro-5-benzyloxyindole hydrochloride, 3-(2-dimethylaminoethyl)-4-chloro-5-n-propyloxy-indole fumarate, 3-(2-aminoethyl)-4-chloro-5-n-propyloxyindole fumarate 3-(2-dimethylaminoethyl)-4-chloro-5-benzyloxyindole hydrochloride, 3-(2-dimethylaminoethyl)-4 -chloro-5-hydroxyindole oxalate, 3-(2-dimethylaminoethyl)-4-chloro-5-methoxyindole fumarate, 3-(2-aminoethyl)-4-chloro-5-methoxyindole fumarate, 3-(2-dimethylaminoethyl)-4-bromo-5-methoxyindole hemifumarate, 3-(2-n-propylaminoethyl)-4-chloro-5-methoxyindole fumarate, 3-(2-methylaminoethyl)-4 -chloro-5-methoxy indolehemi fumarate, 3-(2-dimethylaminoethyl)-4-chloroindole fumarate, 3-(2-dimethylaminoethyl)-4-chloro-5-n-butyloxyindole hemifumarate, 3-(2-pyrrolidinylethyl)-4 -chloro-5-methoxyindole hemifumarate, 3-(2-methylaminoethyl)-4-chloro-5-n-propoxyindole hemifumarate, 3-(2-dimethylaminoethyl)-4-bromo-5-n-propoxyindole hemifumarate, 3-(2-aminoethyl)-4-chloro-5-iso-propoxyindole fumarate, 3-(2-aminoethyl)-4-bromo-5-n-propoxyindole oxalate, 3-(2-dimethylaminoethyl)-4-chloro-5-isopropoxyindole oxalate, 3-(2-(dimethylamino)ethyl)-4-methyl-5-n-propyloxy indole, 3-(2-aminoethyl)-4-methyl-5-n-propyloxyindole oxalate, 3-(2-(N-methyl-N-ethylamino)ethyl)-4-chloro-5-n-propyloxy-indole oxalate, 3-(2-(dimethylamino)ethyl)-4-iodo-5-n-propyloxy indole oxalate, 3-(2-(dimethylamino) ethyl)-4-chloro-5-cyclopropylmethyloxy indole oxalate, and 3-(2-(dimethylamino) ethyl)-4-chloro-5-neopentyloxy indole oxalate.

Pharmaceutically acceptable acid addition salts of the compounds of structure (I) include, for example, those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of formula (I), and are included within the scope of this invention. Also included within the scope of the invention are solvates and hydrates of compounds of formula (I).

It will be appreciated that certain compounds of structure (I) for example where $R^3$ is other than hydrogen may contain an assymetric centre. Such compounds will exist as two (or more) optical isomers (enantiomers). Both the pure enantiomers, racemic mixtures (50% of each enantiomer) and unequal mixtures of the two, are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides, in a further aspect, a process for the preparation of a compound of structure (I) or a salt, solvate or hydrate thereof, which comprises:

(a) reduction of a compound of structure (II):

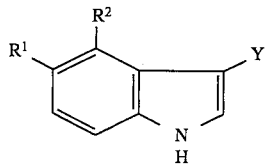

Structure (II)

(in which $R^1$ and $R^2$ are as described for structure (I) and Y is a reducible group) optionally in the presence of a compound of the formula $R^4R^5NH$ in which $R^4$ and $R^5$ are as described for structure (I);

(b) Reaction of a compound of structure (III):

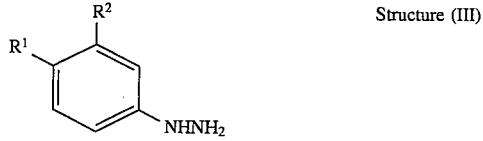

Structure (III)

(wherein $R^1$ and $R^2$ are as hereinbefore defined) or a salt thereof, with a compound of structure (IV):

Structure (IV)

or a protected derivative (e.g. an acetal or ketal) thereof.

converting a group $R^1$ into another group $R^1$;

converting a group $R^2$ into another group $R^2$;

forming a pharmaceutically acceptable salt or hydrate thereof.

In compounds of structure (II) Y may be a group which is converted to —CH($R^3$) $CH_2NR^4R^5$ when reduced in the presence of $R^4R^5NH$, in which case examples of Y include —CH ($R^3$)CN; and —CH ($R^3$)CHO. Alternatively Y may be a group which itself can be reduced to —CH ($R^3$) $CH_2NR^4R^5$, such groups including —CH ($R^3$) $CH_2NO_2$, —CH ($R^3$) $CH_2N_3$, —COCONR$^4$R$^5$, —CH ($R^3$) CONR$^4$R$^5$ and —CH ($R^3$) $CH_2NR^4COR^5$.

It will be appreciated that the precise method of reduction will depend on the nature of the group Y, such methods being well known in the art.

When Y represent —CH ($R^3$) CHO or —CH ($R^3$) CN the reaction between a compound of structure (II) and an amine $R^4R^5NH$ is carried out under reductive amination conditions, for example, catalytic hydrogenation in the presence of the amine $R^4R^5NH$ and a suitable solvent. Suitable catalysts include, for example, Raney nickel. Suitable solvents include, for example, $C_{1-4}$alkanols, in particular methanol. The reaction is carried out at ambient temperature or elevated temperature for as long as is necessary for the reaction to be complete. Preferred reaction conditions include, for example for compounds in which $R^4$ and $R^5$ are both hydrogen, hydrogenation in methanolic ammonia in the presence of a Raney nickel catalyst; and where $R^4$ and $R^5$ are both $C_{1-4}$alkyl, for example methyl, hydrogenation in the presence of dimethylamine in methanol as solvent and Raney nickel as catalyst.

When Y represents a group —CH ($R^3$)CH$_2$NO$_2$, —CH ($R^3$)CH$_2$N$_3$—COCONR$^4$R$^5$, or —CH ($R^3$)CONR$^4$R$^5$ the reduction may be effected for example using allane (prepared from lithium aluminium hydride and sulphuric acid) or lithium aluminium hydride in a solvent such as tetrahydrofuran. Alternatively a group —(CH ($R^3$)CH$_2$NO$_2$ may be reduced by catalytic hydrogenation, using for example palladium on charcoal.

Reduction of a group —CH ($R^3$)CH$_2$NR$^4$COR$^5$ may be accomplished using a hydride such as aluminium hydride.

It will be appreciated that a variety of other substituents Y and methods of reduction are well-known in tryptamine chemistry, such as those described in GB 2185020A, and may also be employed in process (a).

The intermediate compounds of structure (II) can be prepared by standard procedures.

Thus, compounds of structure (II) wherein Y represents —CH$_2$CN may be prepared from the corresponding gramine (i.e. 3-dimethylaminomethyl) compound by cyanation e.g. using potassium cyanide. The gramine derivative may be obtained by reaction of the 3-unsubstituted indole with bisdimethylaminomethane in the presence of acetyl chloride and in a suitable solvent, such as dichloromethane. A 3-unsubstituted indole may be prepared from an appropriately substituted nitrotoluene derivative according to the following reaction scheme 1:

Scheme 1

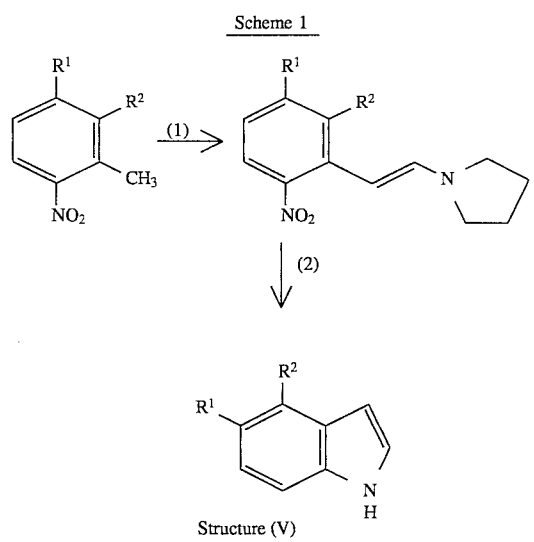

(1) Me$_2$NCH (OEt)$_2$, DMF, pyrrolidine
(2) N$_2$H$_4$.H$_2$O, Ni.

Alternatively a 3-unsubstituted indole may be obtained from an appropriately substituted benzaldehyde derivative according to the following reaction scheme 2:

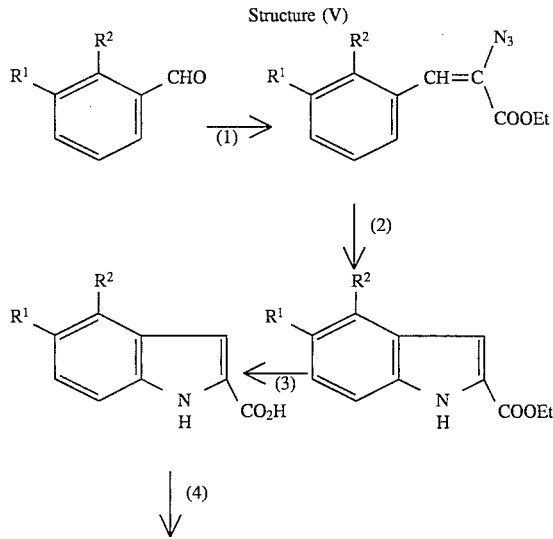

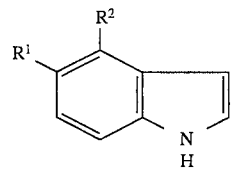

(1) Ethyl azidoacetate/sodium ethoxide/ethanol
(2) toluene, (reflux)
(3) (i) Ethanol/sodium hydroxide (ii) HCl
(4) heating.

When Y represents —CH (R$^3$)CH$_2$NR$^4$COR$^5$ a compound of structure (II) may be prepared by reacting a corresponding aminoethyl compound with an acylating agent, for example an anhydride such as acetic or propionic anhydride or a mixture of an acid with an anhydride e.g. formic acid and acetic anhydride. This intermediate provides a convenient method of preparing compounds of structure (I) wherein one of R$^4$ and R$^5$ is hydrogen and the other a C$_{1-4}$alkyl group.

A compound of structure (II) wherein Y represents —COCONR$^4$R$^5$ may be prepared from an indole of structure (VI)

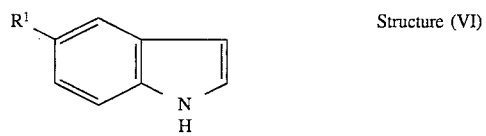

Structure (VI)

by reaction with oxalyl chloride followed by an amine HNR$^4$R$^5$ and subsequently introducing the group R$^2$. When R$^2$ is halogen e.g. iodine this may be introduced by reaction with an appropriate halide e.g. potassium iodide in an acidic medium such as trifluoroacetic acid in the presence of thallium trifluoroacetate.

A compound of structure (II) wherein Y represents —CH(R$^3$)CHO may be prepared for example by oxidation of the corresponding alcohol, using an oxidising agent such as pyridinium chlorochromate, or dimethylsulphoxide with oxalylchloride and triethylamine.

The alcohol may itself be obtained by a cyclisation analogous to process (b). The alcohol may also be converted to a halide derivative and thence to an azide using standard procedures, to give a compound of structure (II) wherein Y represents —CH (R$^3$) CH$_2$N$_3$.

Cyclisation according to process (b) is a standard method for preparing indole compounds and may be effected by methods well known in the art, for example by heating a compound of structure (III) with a compound of structure (IV) in a non-aqueous solvent such as acetic acid or an aqueous or non-aqueous solvent e.g. an alcohol such as methanol in the presence of an acid catalyst such as hydrochloric acid or a Lewis acid such as boron trifluoride, or in the presence of an acidic ion exchange resin.

A compound of structure (III) may be obtained from the corresponding aniline derivative by diazotisation, for example using sodium nitrite and concentrated hydrochloric acid, and subsequent reduction.

Suitable interconversions of R$^1$ groups, and of R$^2$ groups, will be apparent to those skilled in the art and can be carried out by standard procedures. For example, compounds in which R$^1$ is hydroxy can be prepared by deprotection of the corresponding compound in which R$^1$ is a 'protected' hydroxy group such as an arylC$_{1-4}$alkoxy group (such as a benzyl group) or a C$_{1-4}$alkoxy group (such as a methyl group). Suitable conditions and reagents will depend on the nature of the group $R^1$ to be converted, for example when $R^1$ is benzyloxy, conversion to hydroxy can be achieved by hydrogenation over a noble metal catalyst such as palladium on carbon.

Acid addition salts of compounds (I) can be prepared by standard procedures, for example, by reaction with suitable organic and inorganic acids, the nature of which will be apparent to persons skilled in the art.

Compounds of structure (I) have been found to be agonists at $5\text{-}HT_1$-like receptors and certain of them are also agonists at $5\text{-}HT_2$ receptors; they are expected to have utility in medicine in the treatment and/or prophylaxis of migraine, and other conditions associated with cephalic pain, such as cluster headache and headache associated with vascular disorders. Whilst not wishing to be bound by theory, it is believed that $5HT_1$-like agonists are effective in migraine through constriction of cerebral arteries and that $5HT_2$ agonists constrict the superficial temporal artery.

Preferred compounds for use in the treatment and/or prophylaxis of migraine are partial agonists at $5\text{-}HT_1$-like receptors, and, where applicable, $5\text{-}HT_2$ receptors.

Compounds of structure (I) are also expected to have utility in medicine in the treatment or prophylaxis of portal hypertension. Whilst not wishing to be bound by theory, it is believed that $5\text{-}HT_1$-like agonists and $5\text{-}HT2$-agonists are effective in portal hypertension through constriction of mesenteric arterioles, and partial constriction of paraesophageal collaterals with consequent reduction of portal flow and portal pressure. Preferred compounds for use in the treatment of portal hypertension are partial agonists at $5\text{-}HT_2$ receptors and/or $5\text{-}HT_1$-like receptors.

In a further aspect, the invention provides a method of treatment of conditions where a $5\text{-}HT_1$-like or $5\text{-}HT_2$ receptor agonist is indicated in particular migraine or portal hypertension which comprises administering to a subject in need thereof an effective amount of a compound of structure (I) or a pharmaceutically acceptable salt, solvate or hydrate thereof.

For use in medicine, the compounds of the present invention are usually administered in a standard pharmaceutical composition. The present invention therefore provides in a further aspect pharmaceutical compositions comprising a compound of structure (I) or a pharmaceutically acceptable salt, solvate or hydrate thereof and a pharmaceutically acceptable carrier.

The compounds of the invention may be administered by any convenient route, for example by oral, parenteral, buccal, sublingual, nasal, rectal or transdermal administration and the pharmaceutical compositions adapted accordingly.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, preferably between 10 mg and 400 mg e.g. between 10 mg and 250 mg, or an intravenous, subcutaneous, or intramuscular dose of between 0.1 mg and 100 mg, preferably between 0.1 mg and 50 mg e.g. between 1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

BIOLOGICAL DATA $5\text{-}HT_1$-Like Receptor Screen

Dog Saphenous Vein

Helicoids of dog saphenous vein were set up at 37° C. in modified Krebs solution at a resting force of 10 mN. The solution also contained 1 μmol/l each of ketanserin, prazosin, atropine and mepyramine, 6 μmol/l cocaine and 200

µmol/l ascorbate. Nearly isomeric contractions were measured with force transducers on a polygraph. The tissues were exposed twice to 5-hydroxytryptamine (5-HT) 2 µmol/l followed by washes. A cumulative concentration-effect curve to the test compound was determined, followed by a curve to 5-HT in the presence of the highest used concentration of test compound. Contractions caused by the test compound were compared with those caused by 5-HT. The intrinsic activity of the test compound was calculated as the ratio of the maximum test compound-induced effect over the effect caused by 2 µmol/l 5-HT. The $EC_{50}$ of the test compound was estimated from the corresponding effect curve. When appropriate equilibrium dissociation constants Kp were estimated by the method of Marano & Kaumann (1976, J. Pharmacol. Exp. Ther. 198, 518–525).

Compounds of structure (I) were found to be active in this screen, for example the compounds of Examples 1, 2, 3(i) and (ii), 5, 6(i) and (ii), 7, 8, 9, 11, 13, 14, 15, 16 and 17 had $EC_{50}$ values in the range 0.2 to 15 µM.

RABBIT BASILAR ARTERY

Experiments were performed in intracranial arteries from rabbit isolated basilar artery in a similar method to one described previously (Parsons and Whalley, 1989. Eur J Pharmacol 174, 189–196.).

In brief, rabbits were killed by overdose with anaesthetic (sodium pentobarbitone). The whole brain was quickly removed and immersed in ice cold modified Kreb's solution and the basilar artery removed with the aid of a dissecting microscope. The Krebs solution was of the following composition (mM) $Na^+$ (120); $K^+$ (5); $Ca^{2+}$ (2.25); $Mg^{2+}$ (0.5); $Cl^-$ (98.5); $SO_4^{2-}$ (1); EDTA (0.04), equilibrated with 95% $O_2$/5% $CO_2$. The endothelium was removed by a gentle rubbing of the lumen with a fine metal wire. Arteries were then cut into ring segments (ca 4–5 mm wide) and set up for recording of isometric tension in 50 ml tissue baths in modified Krebs solution with the additional supplement of (mM); $Na^{2+}$ (20); fumarate (10); pyruvate (5); L-glutamate (5) and glucose (10). The arteries were then placed under a resting force of 3–4 mN maintained at 37° C. and the solution bubbled with 95% $O_2$/5% $CO_2$.

After tests for initial reactivity with 90 mM KCl depolarising solution and for lack of acetylcholine-induced relaxation of 5-HT (10 mM) precontraction, cumulative concentration-effect curves (2 nM–60 mM) to 5-HT were constructed in the presence of ascorbate 200 mM, cocaine 6 mM, indomethacin 2.8 mM, ketanserin 1 mM and prazosin 1 mM.

Following a 45–60 min wash period, cumulative concentration-effect curves to the test compounds or 5-HT (as a time match control) were constructed in the presence of ascorbate, indomethacin, cocaine, ketanserin and prazosin.

In this screen the compounds of Examples 2, 3(i), 4, 5, 6(i), 11, 14, 18b, 19, 20 and 22 had $EC_{50}$ values in the range 0.17 to 1.1 µMol.

5-HT$_2$-Receptor Screen

Rat Tail Artery (Kaumann A. J. & Frenken M. 1988, J. Pharmacol. Exp. Pharmacol. 245, 1010–1015)

The ventral caudal artery was used from rats pretreated with reserpine 7 mg/kg ip (20 h). Five interconnected arterial rings were prepared and set up to contract in modified Krebs solution at 32.5° C. as follows. Resting force of the rings was set to be 4 mN and the rings allowed to relax thereafter without further readjustment. Three cumulative concentration-effect curves were determined, the first to 5-HT followed by washout, the second to the test compound and the third to 5-HT in the presence of the highest used concentration of test compound. The intrinsic activity of the test compound was calculated as the ratio of the maximum test compound-induced effect over maximum 5-HT-induced effect. The $EC_{50}$ of the test compound was estimated from the corresponding concentration-effect curve. Equilibrium dissociation constants Kp were estimated by the method of Marano & Kaumann (1976, J. Pharmacol. Exp. Ther., 198, 518–525).

In this screen, the compound of Example 5 had an $EC_{50}$ of 0.2 µM.

EXAMPLE 1

3-(2-(Aminoethyl)-4-chloro-5-benzyloxyindole hydrochloride (a) A solution of 2-chloro-3-methyl-4-nitrophenol (30.0g, 0.160 mol) in sieve-dried DMF (650 ml) was treated with sodium hydride (50%, 8.44g, 0.176 mol) and then benzyl bromide (30.1 g, 0.176 mol), while stirring at 0° C. The mixture was stirred at room temperature for 16 hours, then poured into 3 litres of water to precipitate an orange-coloured solid, which was recrystallised from ethanol to give 2-chloro-3-benzyloxy-6-nitrotoluene (31.3 g) m.p. 73°–74.5° C.

(b) To a solution of 2-chloro-3-benzyloxy-6-nitro-toluene (5.00 g, 18.0 mmol) in DMF (25 ml) was added dimethylformamide diethyl acetal (3.14 g, 21.3 mmol) and pyrrolidine (1.51 g, 21.3 mmol), and the mixture was heated at 110° C. for 3 hours under nitrogen. Evaporation under high vacuum at 70° C. gave a deep-red oil which was dissolved in THF (35 ml) and methanol (35 ml) and treated with Raney nickel (0.4 ml) and then hydrazine hydrate (1.30 ml), while stirring at room temperature under nitrogen. The temperature rose to 45° C., and was maintained there by gently warming on an oil bath. A further quantity of hydrazine hydrate (1.30 ml) was added after 30 minutes, and stirring at 45° C. was continued for another hour. The mixture was allowed to cool, filtered through celite, evaporated to a brown oil and purified by chromatography ($SiO_2$; $C_6H_{14}$/$CHCl_3$) to give 4-chloro-5-benzyloxyindole as a yellow oil (3.58 g).

(c) Acetyl chloride (6.42 g, 81.7 mmol) was added dropwise to a stirred solution of bis-dimethylamino-methane (BDAM) (8.34 g, 81.7 mmol) in dry dichloromethane (100 ml), while cooling in an ice bath. After 5 minutes, a solution of 4-chloro-5-benzyloxyindole (15.6 g, 60.7 mmol) in dichloromethane (100 ml) was added, dropwise, followed by addition of 10% aqueous sodium hydroxide (300 ml) after a further 10 minutes. The mixture was extracted with dichloromethane, and the extracts dried ($Na_2SO_4$) and stripped to a crude solid which was purified by chromatography ($SiO_2$; $CHCl_3$/MeOH/$NH_4OH$) and recrystallised from ethanol to give 3-dimethylaminomethyl-4-chloro-5-benzyloxyindole (9.66 g), m.p. 137°–9° C.

(d) Potassium cyanide (7.36 g, 113 retool) was added to a solution of 3-dimethylaminomethyl-4-chloro-5-benzyloxy-indole (9.30 g, 29.5 mmol) in sieve-dried DMF (150 ml). Methyl iodide (17.2 g, 121 mmol) was added dropwise, while stirring over 15 minutes, and stirring was continued for a further hour. The mixture was poured into 10% aqueous sodium sulphate and extracted with diethyl ether. The combined extracts were dried ($Na_2SO_4$) and evaporated to dryness leaving an oil which crystallised. Recrystallisation from methanol gave 3-cyanomethyl-4-chloro-5-benzyloxyindole (5.56 g), m.p. 130°–2° C.

(e) A solution of 3-cyanomethyl-4-chloro-5-benzyloxyindole (1.00 g, 3.37 mmol) in methanolic ammonia (30 ml) was hydrogenated over Raney nickel for 2½ hours at room temperature, at 30 p.s.i. pressure. After filtering off the catalyst, the filtrate was evaporated to give 3-(2-aminoethyl)-4-chloro-5-benzyloxyindole as an oil (1.05 g, 100%). Part of this product (170 mg, 0.57 mmol) was treated with excess ethereal HCl, and the mixture was evaporated to dryness to leave a pink solid, which was recrystallised from ethanol/ether to give 3-(2-amino-ethyl)-4-chloro-5-benzyloxyindole hydrochloride (108 mg) m.p. 224°–5° C.

EXAMPLE 2

3-(2-Aminoethyl)-4-chloro-5-hydroxyindole fumarate

Product from 1(e) (free base, 639 mg, 2.12 mmol) was dissolved in methanol (60 ml) and hydrogenated over Pd-C catalyst (10%, 300 mg) at room temperature, at 25 p.s.i. pressure for 30 minutes. After filtering off the catalyst, the filtrate was evaporated and chromatographed ($SiO_2$; EtOAc/MeOH/$NH_4OH$) to give product free base, which was treated in methanol with fumaric acid (150 mg), then with diethyl ether, and the mixture left at 0° C. overnight, to yield 3-(2-aminoethyl)-4-chloro-5-hydroxy-indole fumarate (111 mg) m.p. 146°–8° C.

EXAMPLE 3

(i) 3-(2-Dimethylaminoethyl)-4-chloro-5-n-propyloxyindole fumarate and (ii) 3-(2-aminoethyl)-4-chloro-5-n-propyloxyindole fumarate (a) Treatment of 2-chloro-3-methyl-4-nitrophenol (15.5 g, 82.7 mmol) with sodium hydride (50%, 4.37 g, 91.0 mmol) and n-propyl bromide (11.2 g, 91.0 mmol) in DMF (300 ml) and subsequent workup as described in 1 (a) gave 2-chloro-3-n-propyloxy-6-nitrotoluene (8.50 g), m.p. 42°–3° C.

(b) Reaction of 2-chloro-3-n-propyloxy-6-nitrotoluene (8.50 g, 37.0 mmol) with dimethylformamide diethyl acetal (6.43 g, 43.7 mmol) and pyrrolidine (3.11 g, 43.7 mmol) in DMF and subsequent workup, as described in 1 (b), followed by treatment with hydrazine hydrate (2×2.7 ml) and Raney nickel (3.9 ml) in THF (70 ml) and methanol (70 ml), gave 4- chloro-5-n-propyloxyindole as an oil (1.37 g).

(c) Treatment of 4-chloro-5-n-propyloxyindole (5.10 g, 24.3 mmol) with bis (dimethylamino)methane (BDAM) (3.34 g, 32.7 mmol) and acetyl chloride (2.57 g, 32.7 mmol) in dichloromethane by the method described in 1 (c) gave 3-dimethylaminomethyl-4-chloro-5-n-propyloxyindole (5.11 g) as a sticky solid.

(d) Reaction of 3-dimethylaminomethyl-4-chloro-5-n-propyloxyindole (3.50 g, 13.1 mmol) with potassium cyanide (3.28 g, 50.4 mmol) and methyl iodide (7.44 g, 52.4 mmol) in DMF by the method described in 1 (d) gave 3-cyanomethyl-4-chloro-5-n-propyloxyindole as an oil which crystallised on standing (2.53 g).

(e) Hydrogenation of 3-cyanomethyl-4-chloro-5-n-propyl-oxyindole (1.50 g, 6.03 mmol) in methanol (75 ml) over Raney nickel at 15 p.s.i. pressure, at room temperature for 1½ hours in the presence of dimethylamine (15 ml), followed by removal of the catalyst by filtration gave a crude product. This was purified by chromatography ($SiO_2$; $CHCl_3$/MeOH) to give two components. The less polar component was treated with fumaric acid (1.1 g) in methanol, then evaporated to dryness, followed by crystallisation first from acetonitrile, then from ethyl acetate/isopropanol to give 3-(2-dimethylaminoethyl)-4-chloro-5-n-propyloxyindole fumarate (279 mg), m.p. 198°–200° C. The more polar component, treated in a similar way provided 3-(2-aminoethyl)-4-chloro-5-n-propyloxyindole fumarate (438 mg), m.p. 183°–5° C.

EXAMPLE 4

3-(2-Dimethylaminoethyl)-4-chloro-5-benzyloxyindole hydrochloride

Product from 1 (d) (1.00 g, 3.37 mmol) was hydrogenated at 15 p.s.i. pressure over Raney nickel in saturated methanolic dimethylamine for one hour at room temperature. The resulting crude mixture was purified by column chromatography ($SiO_2$; $CHCl_3$/MeOH) and treated with ethereal HCl. The resulting mixture was evaporated to dryness and triturated under diethyl ether to give 3-(2-dimethylaminoethyl)-4-chloro-5-benzyloxyindole hydrochloride (0.51 g), m.p. 156°–160° C.

EXAMPLE 5

3-(2-Dimethylaminoethyl)-4-chloro-5-hydroxyindole oxalate

Hydrogenation of 3-(2-dimethylaminoethyl)-4-chloro-5-benzyloxyindole (0.95 g, 2.89 mmol) over Pd-C (10%, 0.40 g) in methanol (50 ml) at 30 p.s.i. pressure for 40 minutes at room temperature, followed by removal of catalyst by filtration and treatment with excess oxalic acid in methanol, then ether gave 3-(2-dimethylaminoethyl)-4-chloro-5-hydroxyindole oxalate as a crystalline solid. Further recrystallisation from methanol/diethyl ether gave 103 mg, m.p. 137° C. dec.

EXAMPLE 6

(i) 3-(2-Dimethylaminoethyl )-4-chloro-5-methoxyindole fumarate (ii) and 3-(2-aminoethyl)-4-chloro-5-methoxyindole fumarate (a) 2-Chloro-3-methyl-4-nitrophenol (9.39 g, 50.0 mmol) was reacted with sodium hydride (50%, 2.64 g, 55.0 mmol) and methyl iodide (7.81 g, 55.0 mmol) in dry DMF (200 ml) by the method described in 1 (a). After treatment with water, the product was extracted with chloroform, and the dried extract evaporated to dryness, leaving an oil which crystallised on cooling, leaving solid 2-chloro-3-methyl-4-nitroanisole (8.19 g).

(b) After reaction of 2-chloro-3-methyl-4-nitroanisole (32.1 g, 159 mmol) with dimethylformamide dimethylacetal (22.6 g, 190 mmol) and pyrrolidine (13.4 g, 188 mmol) in DMF (150 ml) at 120°–140° C. for 1 hour under a slow current of nitrogen, the volatile components were removed under vacuum. To the residue was added dichloromethane (90 ml) and methanol (360 ml) and the solution was evaporated to about half its original volume by heating on a steam bath. After cooling, the solution was left refrigerated overnight to yield 2-nitro-5-methoxy-6-chloro-β-pyrrolidinostyrene as red crystals (33.9 g) m.p. 89°–92° C.

(c) A solution of 2-nitro-5-methoxy-6-chloro-β-pyrrolidinostyrene (5.28 g, 18.7 mmol) in benzene (100 ml) was stirred under nitrogen at 20° C. Raney nickel (0.50 ml) was added, followed by hydrazine hydrate (1.6 ml). After 30 minutes, more hydrazine hydrate was added (1.6 ml), and the mixture was stirred for a further 1½ hours. After filtration through celite, the filtrate was evaporated to dryness to leave a dark yellow crystalline residue, which was purified by chromatography (SiO$_2$; CHCl$_3$), then recrystallised from benzene/hexane to give 4-chloro-5-methoxyindole (2.85 g) m.p. 112°–3° C.

(d) Treatment of 4-chloro-5-methoxyindole (1.97 g, 10.8 mmol) with BDAM (1.48 g, 14.5 mmol) and acetyl chloride (1.14 g, 14.5 mmol) in dry dichloromethane and subsequent workup, as described in 1 (c) gave 3-dimethylaminomethyl-4-chloro-5-methoxyindole (2.05 g) m.p. 145–9° C.

(e) Reaction of 3-dimethylaminomethyl-4-chloro-5-methoxy-indole (2.00 g, 8.40 mmol) with potassium cyanide (2.08 g, 32.0 mmol) and methyl iodide (4.72 g, 33.0 mmol) and subsequent workup as described in 1 (d) gave 3-cyanomethyl-4-chloro-5-methoxyindole (1.69 g), m.p. 138°–9° C.

(f) Reductive amination of 3-cyanomethyl-4-chloro-5-methoxyindole (3.82 g, 17.3 mmol) in methanol (200 ml) and dimethylamine (40 ml) over Raney nickel for 2½ hours at 15 p.s.i. pressure, at room temperature, followed by removal of catalyst and solvent gave a crude product containing two major components. Separation by chromatography (SiO$_2$; CHCl$_3$/MeOH) gave two products. Part of the less polar product (650 mg of 2.13 g) was dissolved in methanol and treated with a solution of excess fumaric acid in methanol. On treatment with diethyl ether and refrigeration, the product, 3-(2-dimethylaminoethyl)-4-chloro-5-methoxyindole fumarate (494 mg) crystallised out, m.p. 223°–5° C. The whole of the more polar product was treated with a solution of oxalic acid in methanol to give 3-(2-aminoethyl)-4-chloro-5-methoxyindole oxalate. Recrystallisation from methanol gave 301 mg, dec > 230° C.

EXAMPLE 7

3-(2-Dimethylaminoethyl)- 4-bromo- 5-methoxyindole hemifumarate

This compound was prepared by the reaction sequence described in 6(a)–(f), starting with 2-bromo-3-methyl-4-nitrophenol. The product had m.p. 233°–234° C.

EXAMPLE 8

3-(2-n-Propylaminoethyl)-4-chloro-5-methoxyindole fumarate (a) A solution of 3-(2-aminoethyl)-4-chloro-5-methoxyindole (260 mg, 1.03 mmol) in propionic anhydride (4 ml) was evaporated to dryness in vacuo at 40° C. Purification by chromatography (SiO$_2$; EtOAc) gave 3-(2-propionyl-aminoethyl)-4-chloro-5-methoxyindole (290 mg).

(b) To dry, distilled THF (12.5 ml) was added with stirring, lithium aluminium hydride (380 mg), followed 5 minutes later by sulphuric acid (490 mg), and the mixture was stirred for a further 10 minutes at room temperature. A solution of 3-(2-propionylaminoethyl)-4-chloro-5-methoxyindole (342 mg, 1.03 μmol) in dry THF was added dropwise to the hydride solution, heated to reflux, and the mixture was heated under reflux for a further 2 minutes and allowed to cool. Water was added until effervescence ceased, and THF was evaporated off, leaving a residue which was partitioned between 1N hydrochloric acid and chloroform. The organic phase was separated, dried (Na$_2$SO$_4$) and evaporated to give unreacted starting material. The aqueous phase was filtered through celite, basified with 40% aqueous sodium hydroxide, extracted with chloroform, dried (Na$_2$SO$_4$) and evaporated to give the product free base. Recovered starting material was recycled twice more to give a total of 234 mg of product free base. This product was dissolved in methanol and treated with a methanolic solution of fumaric acid, and then with ethyl acetate. Crystals of 3-(2-n-propylaminoethyl)-4-chloro-5-methoxyindole fumarate were then collected (159 mg) m.p. 215°–217° C.

EXAMPLE 9

3-(2-Methylaminoethyl)-4-chloro-5-methoxyindole hemifumarate (a) To a mixture of formic acid (90%, 1.25 ml) and acetic anhydride (2.75 ml) was added 3-(2-aminoethyl)-4-chloro-5-methoxyindole (220 mg, 0.98 mmol), and the solution was stirred for 10 minutes. Removal of volatile components in vacuo at 30° C. left a residue which was partitioned between aqueous sodium bicarbonate and chloroform. The organic phase was separated, dried (Na$_2$SO$_4$) and evaporated to dryness. Purification by chromatography (SiO$_2$; C$_6$H$_{14}$/CHCl$_3$) gave 3-(2-formylaminoethyl)-4-chloro-5-methoxyindole (176 mg) m.p. 120–121° C.

(b) Reduction of 3-(2-formylaminoethyl)-4-chloro-5-methoxyindole (170 mg, 0.67 mmol) with aluminium hydride, and subsequent workup as described in 8 (b) gave 3-(2-methylamino-ethyl)-4-chloro-5-methoxyindole hemifumarate (75 mg), m.p. 194°–6° C.

EXAMPLE 10

3-(2-Dimethylaminoethyl)-4-chloroindole fumarate (a) 4-Chloroindole (1.0 g, 6.60 mmol) was reacted with BDAM (0.91 g, 8.9 mmol) and acetyl chloride (0.70 g, 8.9 mmol) according to the method described in 1 (c) to give 3-dimethyl-aminomethyl-4-chloroindole as a crude product. This was dissolved in dry DMF (30 ml) and reacted with potassium cyanide (1.65 g, 25.3 mmol) and methyl iodide (4.12 g, 27.1 mmol), and worked up as described in 1 (d) to give 3-cyanomethyl-4-chloroindole (0,604 g), m.p. 134°–136° C.

(b) A solution of 3-cyanomethyl-4-chloroindole (0.50 g, 2.62 mmol) in methanol (29 ml) and dimethylamine (5.7 ml) was hydrogenated at 15 p.s.i. pressure over Raney nickel for 1½ hours at room temperature. Removal of catalyst and solvents left a crude product which was purified by chromatography (SiO$_2$; CHCl$_3$/MeOH) to give two major components. The less-polar component (321 mg) was dissolved in methanol and treated with a methanolic solution of fumaric acid, then with diethyl ether. After standing overnight refrigerated, 3-(2-dimethyl-aminoethyl)-4-chloroindole fumarate was obtained as white needles (0.29 g), m.p. 172.5°–175° C.

EXAMPLE 11

3-(2-Dimethylaminoethyl)-4-chloro-5-n-butyloxyindole hemifumarate (a) 2-Chloro-3-methyl-4-nitrophenol (20.0 g, 107 mmol) was converted to 2-chloro-3-n-butyloxy-6-nitrotoluene by analogy with Example 1 (a) to give a yellow oil (11.7 g).

(b) The above product (11.0 g, 45.1 mmol) was converted to 4-chloro-5-n-butyloxyindole by the procedure described in Example 1 (b), to yield an oil (4.25 g).

(c) The above product (7.23 g, 32.3 mmol) was converted to 3-dimethylaminomethyl-4-chloro-5-n-butyloxyindole by analogy with Example 1 (c) to give the product as a yellow oil (6.37 g).

(d) The above product (6.00 g, 21.4 mmol) was converted to 3-cyanomethyl-4-chloro-5-n-butyloxyindole by analogy with Example 1 (d) to give a solid product (3.27 g).

(e) The above product (2.00 g, 7.61 mmol) was hydrogenated in the presence of dimethylamine, as described for Example 1 (e) to give 3-(2-dimethylamino-ethyl)-4-chloro-5-n-butyloxyindole. This was converted to the hemifumarate in methanol to give a crystalline product, m.p. 202°–204° C. from methanol (0.45 g).

EXAMPLE 12

3-(2-Pyrrolidinylethyl)-4-chloro-5-methoxyindole hemifumarate

3-Cyanomethyl-4-chloro-5-methoxyindole (2.0 g, 9.1 mmol) was reductively aminated with pyrrolidine (32 ml) in methanol (100 ml) over Raney nickel for 2½ hours at 30 p.s.i. pressure, at room temperature. After removal of the catalyst, the solvent was removed and the crude mixture purified by chromatography ($SiO_2$; $CHCl_3$/MeOH) to give 3-(2-Pyrrolidinylethyl)-4-chloro-5-methoxyindole (1.26 g) as a solid. Part of this product (250 mg) was dissolved in methanol (10 ml) and treated with a solution of fumaric acid (150 mg) in methanol (5 ml), then ether to give the product as the hemifumarate salt (244 mg), m.p. 217°–8° C.

EXAMPLE 13

3-(2-Methylaminoethyl)-4-chloro-5-n-propoxyindole hemifumarate

The title compound (90 mg) was prepared in similar manner to Example 9 from 3-(2-aminoethyl)-4-chloro-5-n-propoxyindole fumarate (363 mg). The product had m.p. 212°–214° C.

EXAMPLE 14

3-(2-Dimethylaminoethyl)-4-bromo-5-n -propoxyindole hemifumarate

The title compound (436 mg) was prepared in similar manner to Example 7 from 2-bromo-3-methyl-4-nitrophenol (15.5 g). The product had m.p. 190°–200° C.

EXAMPLE 15

3-(2-Aminoethyl)-4-chloro-5-iso-propoxyindole fumarate

The title compound (550 mg) was prepared in similar manner to Example 3 from 2-chloro-3-methyl-4-nitrophenol (15.0 g). The product had m.p. 185°–187° C.

EXAMPLE 16

3-(2-Aminoethyl)-4-bromo-5-n-propoxyindole oxalate

The title compound (55 mg) was prepared in similar manner to Example 7 from 2-bromo-3-methyl-4-nitrophenol (15.5 g). The product had m.p. 180°–186° C.

EXAMPLE 17

3-(2-Dimethylaminoethyl)-4-chloro-5-isopropoxyindole oxalate

The title compound (512 mg) was prepared in similar manner to Example 3 from 2-chloro-3-methyl-4-nitrophenol (15.0 g). The product had m.p. 179–180° C.

EXAMPLE 18

(a) 3-(2-(Dimethylamino) ethyl)-4-methyl-5-n-propyloxy indole arid (b) 3-(2-aminoethyl)-4-methyl-5-n-propyloxyindole oxalate Sodium hydride (1.15 g, 50% in oil) was added to a stirred solution of 2-methyl-3-hydroxybenzaldehyde (3.00 g) in dry DMF (30 ml). The mixture was stirred for 1 h at room temperature under nitrogen, then n-propyl iodide (4.49 g) was added portionwise over 20 min, followed by stirring for 1 h. The mixture was poured into water and extracted with diethyl ether, and the combined extracts dried ($MgSO_4$) and evaporated to dryness. Purification by chromatography ($SiO_2$; hexane/ethyl acetate) gave 2-methyl-3-n-propyloxybenzaldehyde (1.38 g).

A mixture of the above product (1.3 g) and ethyl azidoacetate (3.77 g) was added to a solution of sodium ethoxide in ethanol (from 0.67 g sodium in 25 ml ethanol) at −10° to −5° C. over 15 min. The resulting orange solution was stirred at this temperature for 1 h, and then allowed to warm to room temperature and left to stand overnight. The mixture was poured into aqueous ammonium chloride solution, and extracted with diethyl ether, and the combined extracts washed with water, then brine, and dried over magnesium sulphate. On removing solvent in vacuo, a solid was obtained, which was purified by chromatography ($SiO_2$; diethyl ether/hexane) to give 1-(2-methyl-3-n-propyloxyphen-1-yl)-2-azido-2-ethoxycarbonyl ethene (1.03 g).

The above azido compound (1.03 g) was dissolved in toluene (100 ml) and the solution was added dropwise to boiling toluene (100 ml) under nitrogen, over 1½ h. The solution was heated under reflux for a further hour, after which the solvent was partially removed in vacuo and the concentrated solution left to crystallize. The crystalline product of 2-ethoxycarbonyl-4-methyl-5-n-propyloxy indole was filtered off and dried (0.93 g).

The above product (0.45 g) was dissolved in a mixture of ethanol (4 ml) and 2M sodium hydroxide solution (2 ml), and the mixture was heated under reflux for 2 h. The resulting solution was evaporated to dryness, and the residue was dissolved in water and treated with dilute HCl. The precipitated solid was filtered off, and washed with chloroform to give 2-carboxy-4-methyl-5-n-propyloxyindole (0.34 g). This product (1.25 g) was decarboxylated by heating at just above its melting point until the evolution of $CO_2$ was complete. The crude reaction mixture was purified by chromatography ($SiO_2$; hexane/ether) to give 4-methyl-5-n-propyloxyindole as an oil (0.62 g).

Reaction of 4-methyl-5-n-propyloxyindole with BDAM to give the gramine derivative, and subsequent cyanation and reductive amination of the indole acetonitrile derivative with dimethylamine by the methods described in example 1 gave a mixture of the two title compounds as their free bases.

These were separated by chromatography. The primary amine was subsequently converted to the oxalate salt, mp 181°–3° C. The tertiary amine product had mp 87°–8° C.

EXAMPLE 19

3-(2-(N-methyl-N-ethyl amino)ethyl)-4-chloro-5-n-propyloxyindole oxalate

3-Cyanomethyl-4-chloro-5-n-propyloxyindole (0.65 g) was dissolved in methanol and hydrogenated over Raney nickel in the presence of N-methyl ethylamine (20 ml) for 2 h at room temperature and 30 psi pressure as described in example 1. After purification by chromatography the product free base was converted to the oxalate salt to give the title compound (0.13 g), mp 142°–3° C.

EXAMPLE 20

3-(2-(Dimethylamino) ethyl)-4-iodo-5-n-propyloxy indole oxalate

Sodium hydride (0.99 g, 50% in oil) was added to dry DMF (5 ml) and the resulting suspension was stirred at room temperature. A solution of 5-hydroxyindole (2.5 g) in dry DMF (15 ml) was added dropwise and a dark purple solution formed. After stirring the mixture for 30 min, 1-iodopropane (3.51 g) was added, and the resulting mixture was stirred at room temperature for 3 h. The mixture was poured into water and extracted with ether ($3x$). The combined extracts were washed with water, dried ($MgSO_4$) and evaporated to dryness to give a crude residue which was purified by chromatography ($SiO_2$; hexane/ether). 5-n-Propyloxyindole was obtained as a yellow oil (2.03 g).

The above product (0.25 g) was dissolved in dry ether (5 ml) and the solution was stirred at room temperature. To this was added oxalyl chloride (0.24 g), which gave an immediate orange-coloured precipitate of 5-n-propyloxy-3-indoleglyoxylyl chloride. The solid product was filtered off and dried (0.27 g).

To a solution of 5-n-propyloxy-3-indoleglyoxylyl chloride (0.27 g) in dichloromethane (15 ml) was added dimethylamine (91 mg). The mixture was evaporated to dryness, and the residue was partitioned between dichloromethane and aqueous potassium carbonate solution. The organic phase was washed with aqueous potassium carbonate solution, dried ($MgSO_4$) and evaporated to an off-white solid of 5-n-propyloxy-3-indole-N,N-dimethyl glyoxylamide (0.25 g).

A solution of thallium trifluoroacetate (0.41 g) in trifluoroacetic acid (1.3 ml) was added to a solution of the above product (0.25 g) in trifluoroacetic acid (0.9 ml), and the mixture was stirred at room temperature for 2 h. The solvent was evaporated, and to the residue was added potassium iodide (1.59 g) in water (10 ml). After standing overnight, sodium carbonate was added to the mixture until no more effervescence occurred. The mixture was filtered, and the dark green residue was dissolved in chloroform and washed with aqueous sodium carbonate solution. The organic phase was washed with aqueous sodium carbonate solution, dried ($MgSO_4$) and evaporated to dryness. The resulting green oil was purified by chromatography ($SiO_2$; $CHCl_{3/10}$% $NH_3$ in MeOH) to give 4-iodo-5-n-propyloxy-3-indole-N,N-dimethyl glyoxylamide as a white solid (from ether) (52 mg).

The above product (430 mg) was dissolved in dry THF (70 ml) and a solution of allane in THF (26.8 ml, 0.4M from lithium aluminium hydride (380 mg) and sulphuric acid (500 mg, 98%) in dry THF (25 ml)) was added. The reaction mixture was stirred at room temperature for 1 h. Water was added dropwise until effervescence ceased. The THF was evaporated and the residue was partitioned between chloroform and 1M HCl. The aqueous phase was then neutralized with 40% aqueous sodium hydroxide solution, and extracted with chloroform, dried ($MgSO_4$), filtered and evaporated to give a brown oil. This was purified by chromatography ($SiO_2$; hexane/ethanol) to give an oil which was treated with oxalic acid in methanol to give the title compound mp 168°–170° C. (148 mg).

EXAMPLE 21

3-(2-(Dimethylamino)ethyl)-4-chloro-5-cyclopropyl-methyloxy indole oxalate

2-Chloro-3-methyl-4-nitrophenol (2.71 g) was reacted with bromomethylcyclopropane (3.89 g) in dry DMF (30 ml) in the presence of potassium carbonate (3.99 g), heating the mixture at 100° C. overnight. The DMF was evaporated in vacuo, and the residue was partitioned between 2M HCl and ethyl acetate. The organic extracts were combined and dried ($MgSO_4$) and evaporated to give 2-chloro-3-cyclopropylmethyloxy-6-nitro toluene (3.26 g).

The above product (3.67 g) was reacted with DMF diethyl acetal (2.64 g) and pyrrolidine (1.29 g) in dry DMF, and the resulting enamine was reductively cyclized using hydrazine hydrate (2.76 g) and Raney nickel in methanol by the method described in example 1to give 4-chloro-5-cyclopropyl-methyloxy indole (0.84 g).

Reaction of 4-chloro-5-cyclopropylmethyloxy indole (1.02 g) with BDAM, and subsequent cyanation and reductive amination of the indole acetonitrile derivative by the methods described in example 1 gave the title compound mp 167°–170° C. (116 mg).

EXAMPLE 22

3-(2-(Dimethylamino) ethyl)-4-chloro-5-neopentyloxy indole oxalate

Reaction of 2-chloro-3-methyl-4-nitrophenol (2.26 g) with neopentyl iodide (4.78 g) in 1-methyl 2-pyrrolidinone (30 ml) in the presence of potassium carbonate (3.34 g) was conducted at 140° C. overnight. The crude product was partitioned between 2M HCl and ethyl acetate, and the organic phase was washed with water, dried ($MgSO_4$) and evaporated to dryness. The residue was chromatographed ($SiO_2$; hexane/ether) to give 2-chloro-3-neopentyloxy-6-nitrotoluene as a yellow solid (2.44 g).

The above product (2.63 g) was reacted with DMF diethyl acetal (1.78 g) and pyrrolidine (0.86 g) in dry DMF, and the resulting enamine was reductively cyclized using hydrazine hydrate (1.86 g) and Raney nickel in methanol by the method described in example 1to give 4-chloro-5-neopentyloxy indole (1.11 g).

Reaction of 4-chloro-5-neopentyloxy indole (1.10 g) with BDAM, and subsequent cyanation, and reductive amination of the indole acetonitrile derivative by the methods described in example 1 gave the title compound, mp 180°–4° C. (55 mg).

PHARMACEUTICAL FORMULATIONS

EXAMPLE A

A tablet for oral administration is prepared by combining

|  | Mg/Tablet |
| --- | --- |
| Compound of formula (I) | 100 |
| lactose | 153 |
| starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration is prepared from the following

|  | % w:w |
| --- | --- |
| Compound of formula (I) | 0,50% (w:v) |
| 1M citric acid | 30% (v:v) |
| sodium hydroxide (qs) | to pH 3.2 |
| water for injection BP | to 100 ml |

The compound of formula (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

We claim:

1. A method of treatment of condition where a 5-$HT_1$-like or 5-$HT_2$ receptor agonist is indicated which comprises administering to a subject in need thereof an effective amount of a compound of structure (I):

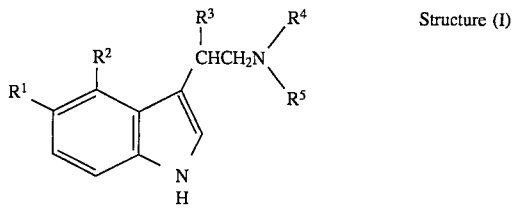

Structure (I)

in which $R^1$ is hydrogen, hydroxy, $C_{1-4}$alkoxy, halo $C_{1-4}$alkoxy, $C_{3-7}$cycloalkyl-$C_{1-4}$alkoxy, aryloxy or aryl$C_{1-4}$alkyl;

$R^2$ is halogen, $C_{1-4}$alkyl, CN, $NO_2$ or $CF_3$;

$R^3$ is hydrogen or $C_{1-4}$alkyl;

$R^4$ and $R^5$ are the same or different and are each hydrogen or $C_{1-4}$alkyl or together with the nitrogen atom to which they are attached form a heterocyclic ring; or a pharmaceutically acceptable salt, solvate or hydrate thereof, provided that the compound of structure (I) is not 3-(2-n-propylaminoethyl)-4-chloro-5-methoxyindole, 3-(2-methylminoethyl)-4-chloro-5-methoxyindole, or 3-(2-methylaminoethyl)4-chloro-5-propoxyindole.

2. The method according to claim 1 wherein the condition is migmine.

3. The method according to claim 1 wherein the condition is portal hypertension.

4. A compound of structure (I) or a salt, solvate or hydrate thereof, wherein $R^1$, $R^2$, $R^3$, $R^4$ and $R^5$ are as defined in claim 1, with the provisos that:

(i) when $R^1$ is hydroxy and $R^3$, $R^4$ and $R^5$ are each hydrogen then $R^2$ is not chloro or methyl;

(ii) when $R^1$ is methoxy and $R^3$, $R^4$ and $R^5$ are each hydrogen then $R^2$ is not $NO_2$; and (iii) when $R^1$, $R^3$, $R^4$ and $R^5$ are each hydrogen then $R^2$ is not bromo, chloro, CN or methyl.

5. The compound according to claim 4 wherein $R^1$ is hydroxy, $C_{1-4}$alkoxy or aryl$C_{1-4}$alkoxy.

6. The compound according to claim 4 wherein $R^2$ is halogen.

7. The compound according claim 4 wherein $R^3$ is hydrogen.

8. The compound according to claim 4 wherein $R^4$ and $R^5$ are each hydrogen or $C_{1-4}$alkyl.

9. The compound according to claim 4 wherein $R^1$ is hydroxy, $C_{1-4}$alkoxy or aryl$C_{1-4}$alkoxy, $R^2$ is halogen, $R^3$ is hydrogen and $R^4$ and $R^5$ are each hydrogen or $C_{1-4}$alkyl.

10. The compound of structure (I) according to claim 1, which is selected from:

3-(2-(aminoethyl)-4-chloro-5-benzyloxyindole;

3-(2-dimethylaminoethyl)-4-chloro-5-n-propyloxy-indole;

3-(2-aminoethyl)-4-chloro-5-n-propyloxyindole;

3-(2-dimethylaminoethyl)-4-chloro-5-benzyloxyindole;

3-(2-dimethylaminoethyl)-4-chloro-5-hydroxyindole;

3-(2-dimethylaminoethyl)-4-chloro-5-methoxyindole;

3-(2-aminoethyl)-4-chloro-5-methoxyindole;

3-(2-dimethylaminoethyl)-4-bromo-5-methoxyindole;

3-(2-dimethylaminoethyl)-4-chloroindole;

3-(2-dimethylaminoethyl)-4-chloro-5-n-butyloxyindole;

3-(2-pyrrolidinylethyl)-4-chloro-5-methoxyindole;

3-(2-dimethylaminoethyl)-4-bromo-5-n-propoxyindole;

3-(2-aminoethyl)-4-chloro-iso-propoxyindole;

3-(2-aminoethyl)-4-bromo-5-n-propoxyindole;

3-(2-dimethylaminoethyl)-4-chloro-5-isopropoxyindole;

3-(2-(dimethylamino)ethyl)-4-methyl-5-n-propyloxyindole;

3-(2-aminoethyl)-4-methyl-5-n-propyloxyindole;

3-(2-(N-methyl-N-ethylamino)ethyl)-4-chloro-5-n-propyloxyindole;

3-(2-(dimethylamino)ethyl)-4-iodo-5-n-propyloxy indole;

3-(2-(dimethylamino)ethyl)-4-chloro-5-cyclopropylmethyloxy indole; and 3-(2-(dimethylamino)ethyl)-4-chloro-5-neopentyloxy indole;

or a salt, hydrate or solvate thereof.

11. A pharmaceutical composition comprising a compound of structure (I) according to claim 1 or a pharmaceutically acceptable salt, solvate or hydrate thereof and a pharmaceutically acceptable carrier.

* * * * *